(12) United States Patent
Thandiackal et al.

(10) Patent No.: US 7,254,216 B2
(45) Date of Patent: Aug. 7, 2007

(54) METHODS AND APPARATUS FOR FILTERING A RADIATION BEAM AND CT IMAGING SYSTEMS USING SAME

(75) Inventors: Lijo Joseph Thandiackal, Waukesha, WI (US); Todd Everett Schueneman, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/192,839

(22) Filed: Jul. 29, 2005

(65) Prior Publication Data

US 2007/0025520 A1 Feb. 1, 2007

(51) Int. Cl.
*G21K 3/00* (2006.01)

(52) U.S. Cl. ............... 378/159; 378/157; 378/158

(58) Field of Classification Search ......... 378/156–159
See application file for complete search history.

(56) References Cited

U.S. PATENT DOCUMENTS

| | | | |
|---|---|---|---|
| 4,181,858 A * | 1/1980 | Moore | 378/18 |
| 4,399,550 A | 8/1983 | Hauck et al. | |
| 4,472,828 A | 9/1984 | Ferlic | |
| 4,528,685 A | 7/1985 | Kump et al. | |
| 4,975,933 A * | 12/1990 | Hampel | 378/5 |
| 5,878,111 A | 3/1999 | Schulz | |
| 5,966,426 A | 10/1999 | Marra et al. | |
| 6,061,426 A | 5/2000 | Linders et al. | |
| 6,118,855 A | 9/2000 | Welters et al. | |
| 6,173,039 B1 * | 1/2001 | Hampel et al. | 378/150 |
| 6,181,774 B1 | 1/2001 | Prins et al. | |
| 6,188,749 B1 | 2/2001 | Schiller et al. | |
| 6,198,806 B1 | 3/2001 | Prins | |
| 6,252,939 B1 | 6/2001 | Young et al. | |
| 6,269,147 B1 | 7/2001 | Powell | |
| 6,275,568 B1 | 8/2001 | Prins et al. | |
| 6,307,918 B1 * | 10/2001 | Toth et al. | 378/158 |
| 6,370,228 B1 | 4/2002 | Mockler et al. | |
| 6,426,999 B2 | 7/2002 | Prins | |
| 6,438,211 B1 | 8/2002 | Weekamp et al. | |

(Continued)

FOREIGN PATENT DOCUMENTS

WO WO 00/02383 1/2000

(Continued)

*Primary Examiner*—Edward J. Glick
*Assistant Examiner*—Anastasia S. Midkiff
(74) *Attorney, Agent, or Firm*—Armstrong Teasdale LLP (57) ABSTRACT

A filter assembly for a computed tomographic imaging system includes first and second endplates at opposite ends of the filter assembly. Also provided is a first moveable subassembly that includes at least a first x-ray filter and which is configured to move along an axis perpendicular to the first endplate between the first the second endplates. A second moveable subassembly is also provided that includes at least a second x-ray filter. The second moveable subassembly is configured to move along an axis perpendicular to the second endplate between the first and second endplates. The first moveable subassembly and the second moveable subassembly are independently movable to provide at least a small bowtie x-ray filter, a large bowtie x-ray filter, a medium bowtie x-ray filter, a flat filter, and a closed position for a radiation source positioned in a fixed position relative to the filter assembly.

21 Claims, 7 Drawing Sheets

U.S. PATENT DOCUMENTS

| | | |
|---|---|---|
| 6,453,012 B2 | 9/2002 | Herbert |
| 6,584,173 B2 | 6/2003 | Zwart et al. |
| 6,775,353 B2 | 8/2004 | Thandiackal et al. |
| 6,778,634 B2 | 8/2004 | Thandiackal et al. |
| 6,814,488 B2 | 11/2004 | Thandiackal et al. |
| 2003/0081727 A1 | 5/2003 | Kandankumarath et al. |
| 2004/0136500 A1 | 7/2004 | Amemiya et al. |
| 2005/0013411 A1* | 1/2005 | Yahata et al. ................ 378/156 |
| 2005/0089146 A1* | 4/2005 | Toth et al. .................. 378/158 |

FOREIGN PATENT DOCUMENTS

| | | |
|---|---|---|
| WO | WO 01/80252 A1 | 10/2001 |
| WO | WO 02/25671 A1 | 3/2002 |

\* cited by examiner

METHODS AND APPARATUS FOR FILTERING A RADIATION BEAM AND CT IMAGING SYSTEMS USING SAME

BACKGROUND OF THE INVENTION

This invention relates generally to CT imaging systems, and more particularly to methods and apparatus for reducing a radiation dose applied to an object or person being imaged.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

Significant dose reduction can be achieved by using a bowtie filter to shape the intensity profile of the x-ray beam in the X-axis. Also, different shaped bowties can be advantageously used. For example, one shape can be used for the head or a small body, yet another shape for a pediatric head and another shape for a large body or flat. A large selection of shapes would be useful to best fit each patient and patient anatomy.

However, manufacturing an imaging system with a large number of bowtie filters can significantly increase the overall cost of the imaging system because of the volume required to accommodate and move each of the filters.

BRIEF DESCRIPTION OF THE INVENTION

The present invention, in one aspect, therefore provides a filter assembly for a computed tomographic imaging system. The filter assembly includes first and second endplates at opposite ends of the filter assembly. Also provided is a first moveable subassembly that includes at least a first x-ray filter and which is configured to move along an axis perpendicular to the first endplate between the first the second endplates. A second moveable subassembly is also provided that includes at least a second x-ray filter. The second moveable subassembly is configured to move along an axis perpendicular to the second endplate between the first and second endplates. The first moveable subassembly and the second moveable subassembly are independently movable to provide at least a small bowtie x-ray filter, a large bowtie x-ray filter, a medium bowtie x-ray filter, a flat filter, and a closed position for a radiation source positioned in a fixed position relative to the filter assembly.

In another aspect, the present invention provides a computed tomographic (CT) imaging system. The CT imaging system includes a rotatable gantry having a gantry opening and an x-ray filter assembly on the rotatable gantry. The CT imaging system also includes a radiation source configured to direct a fan beam of radiation towards an object in the gantry opening through the x-ray filter assembly and a detector array on the rotatable gantry configured to acquire projection data representative of radiation passing through the object. The CT imaging system is configured to reconstruct an image of the object utilizing the acquired projection data. Also, the filter assembly further includes first and second endplates at opposite ends of the filter assembly. Also provided is a first moveable subassembly that includes at least a first x-ray filter and which is configured to move along an axis perpendicular to the first endplate between the first the second endplates. A second moveable subassembly is also provided that includes at least a second x-ray filter. The second moveable subassembly is configured to move along an axis perpendicular to the second endplate between the first and second endplates. The first moveable subassembly and the second moveable subassembly are independently movable to provide at least a small bowtie x-ray filter, a large bowtie x-ray filter, a medium bowtie x-ray filter, a flat filter, and a closed position for a radiation source positioned in a fixed position relative to the filter assembly.

In yet another aspect, the present invention provides a method for filtering a radiation source of a computed tomographic (CT) imaging system for scanning a region of an object using the CT imaging system. The method includes passing a fan beam of the radiation source between first and second endplates at opposite ends of a filter assembly. The filter assembly has a first moveable subassembly that includes at least a first x-ray filter configured to move along an axis perpendicular to the first endplate and the fan beam between the first and second endplates. The filter assembly also has a second moveable subassembly comprising at least a second x-ray filter configured to move along an axis perpendicular to the second endplate and the fan beam between the first and second endplates. The method further includes moving at least one of the first moveable subassembly or the second moveable subassembly to interpose a small bowtie x-ray filter, a large bowtie x-ray filter, a medium bowtie x-ray filter, a flat filter, or a closed position between the radiation source and the object.

Significant dose reduction is achievable by using bowtie filters to shape the intensity profile of the x-ray beam in the X-axis of a CT imaging system. It will be appreciated that configurations of the present invention advantageously accommodate multiple bowtie filters within a given volume. These filters can be accommodated economically and, in at least some CT configurations, without significant configuration changes. Various configurations of the present invention not only accommodate multiple filter configurations but also provide the ability to conveniently change filter configurations.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
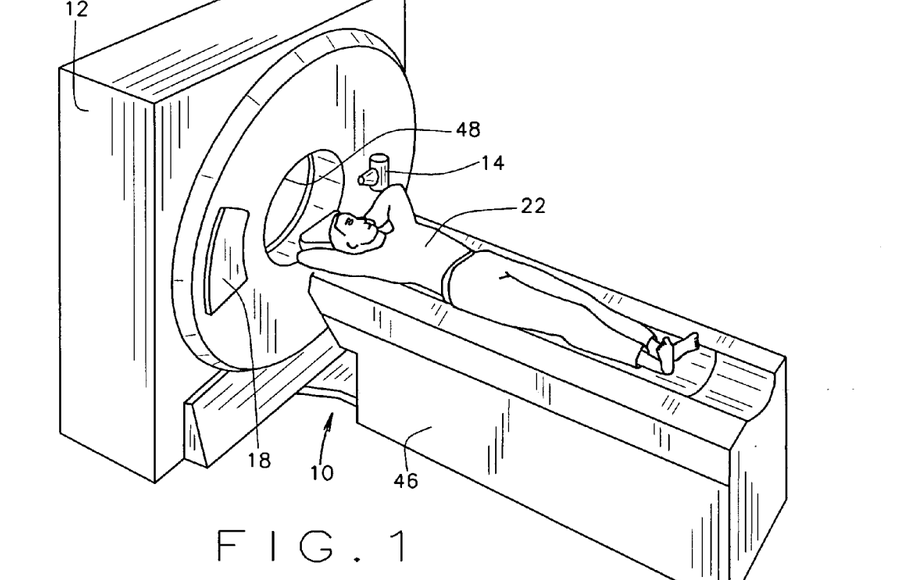
FIG. 1 is a pictorial diagram of a configuration of a CT imaging system in accordance with the present invention.
Figure 2:
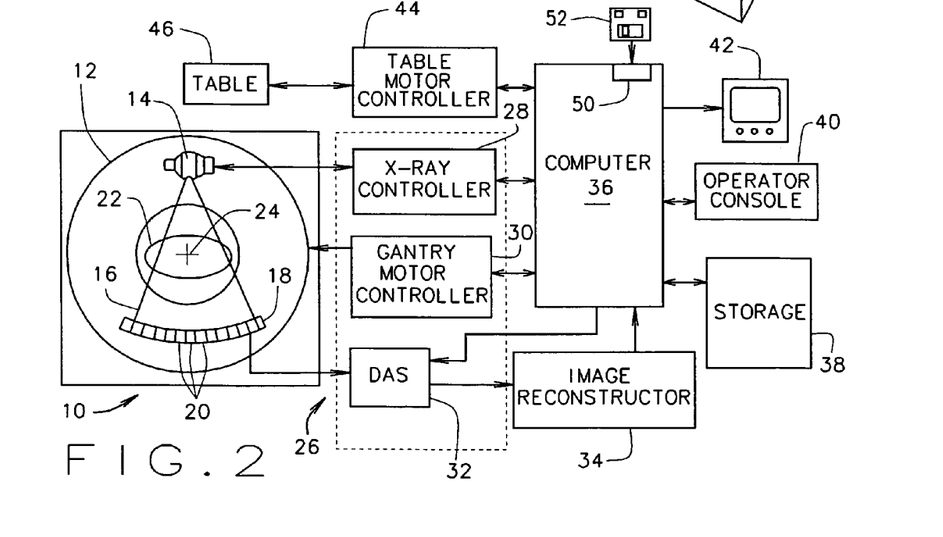
FIG. 2 is a block schematic diagram of the configuration of CT imaging system shown in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has a radiation source 14 (such as an x-ray tube, which is also called an x-ray source herein) that projects a beam of radiation, such as x-rays 16, toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 (or any other suitable type of display, such as a liquid crystal display or plasma display) allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
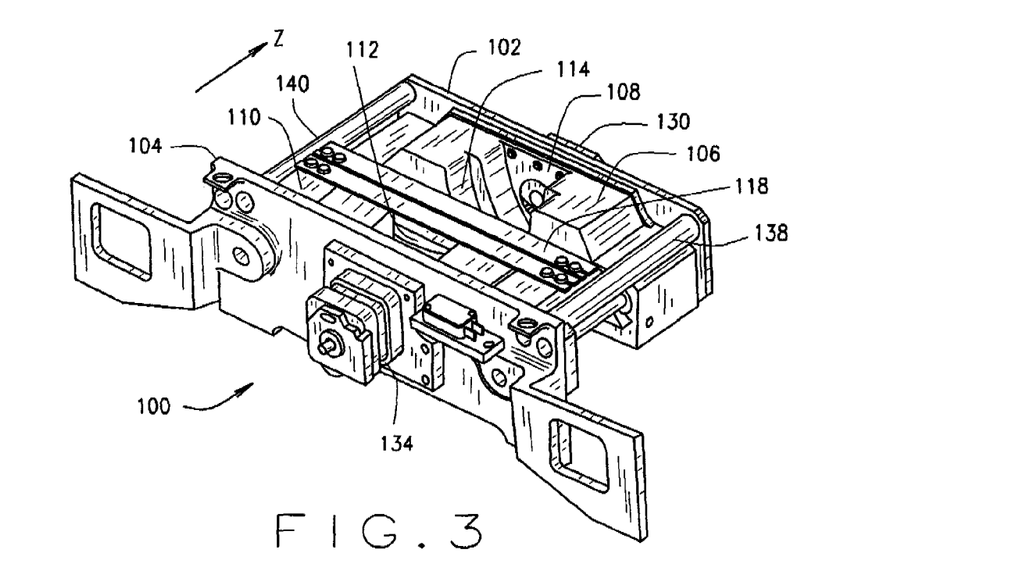
FIG. 3 is a pictorial view representing one configuration of a filter assembly of the present invention.

In some configurations of the present invention and referring to FIG. 3, a filter assembly 100 is provided in an efficient packaging design to provide multiple "bowtie" filters shapes and profiles. Filter assembly 100 includes a first endplate 102 and a second endplate 104 at opposite ends of filter assembly 100. Also included are a first moveable subassembly 106 that includes at least a first x-ray filter 108. First moveable subassembly 106 is configured (for example, in a manner described in more detail below) to move along an axis z perpendicular to first endplate 102 and in a region between first endplate 102 and second endplate 104. Similarly, second moveable subassembly 110 includes at least a second x-ray filter 112. Second moveable subassembly 110 is configured (for example, in a manner similar to that of first moveable subassembly 106) to move along an axis z (e.g., the same axis z as subassembly 106) perpendicular to second endplate 104. Second moveable subassembly 110 is also configured to move in a region between first endplate 102 and second endplate 104. First and second moveable subassemblies 106 and 110 are not required to move through the entire region between endplates 102 and 104, and in fact, the ranges of movement of subassemblies 106 and 110 are each limited in some configurations. In some configurations, subassemblies 106 and 110 are independently moveable to provide a plurality of filters, depending upon which of subassemblies 106 or 110, or both, is positioned within x-ray beam 16.

In some configurations, first moveable subassembly 106 and second moveable subassembly 110 are independently moveable to provide at least a small bowtie x-ray filter 108, a large bowtie x-ray filter 114, a medium bowtie x-ray filter 112, a flat filter 118, and a closed position 120. All of these filters are provided for radiation source 14, which is positioned in a fixed position relative to filter assembly 100.

Also in some configurations, first moveable subassembly 106 includes a small bowtie filter 108 and a large bowtie filter 114, and second moveable subassembly 110 includes a medium bowtie filter 112. Also, at least one flat filter 118 is configurable (for example, by movement of one or more of subassemblies 106 or 110) to overlap a portion of one of bowtie filters 108 and 114 of first moveable subassembly 106 in at least one position in a range of movement of first moveable subassembly 106 and second moveable subassembly 110.

In some configurations, filter assembly 100 includes flat filter 118 and a second flat filter 122. In an exemplary embodiment, second flat filter 122 is a titanium plate, and flat filter plate 118 is a tungsten plate. The one or more bowtie filters 108, 114 of first moveable subassembly 106 can comprise a combination of aluminum and graphite machined parts and copper. The one or more bowtie filters 112 of second moveable subassembly 110 can comprise aluminum and graphite machined parts.

Figure 4:
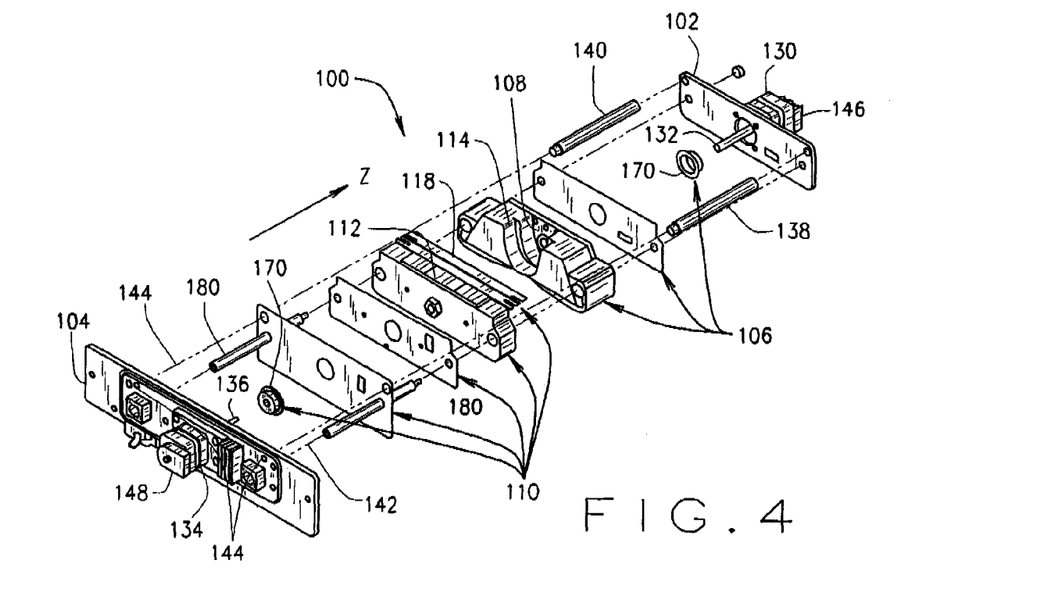
FIG. 4 is an exploded pictorial view of the filter assembly shown in FIG. 3.

To move subassemblies 106 and 110, some configurations of the present invention provide a first stepper motor 130 with a lead screw drive 132 that is configured to move first moveable subassembly 106 and a second stepper motor 134 with a lead screw drive 136 that is configured to move second movable subassembly 110. Hollow tubing 138, 140, such as hollow metal tubing, is provided between first endplate 102 and second endplate 104. Wires or cables 142, 144 are run inside the hollow tubing to carry electrical signals to at least one of stepper motors 130 or 134. One or more position encoders 146, 148 can be provided in some configurations with a feedback control (which can be provided, for example, by computer 36 or by a separate feedback control, not shown in the figures) to provide a home position reference and position feedback. Wires or cables for position encoders 146 and 148 can also be run through hollow tubing 138, 140.

Figure 5:
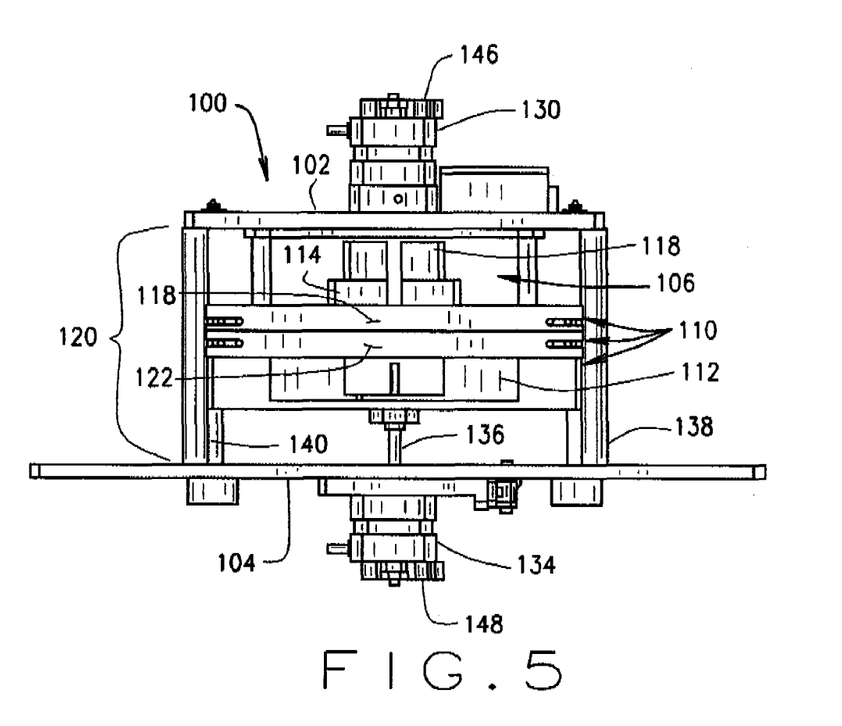
FIG. 5 is a top view of the filter assembly shown in FIG. 3 showing the filter assembly in a closed position.
Figure 8:
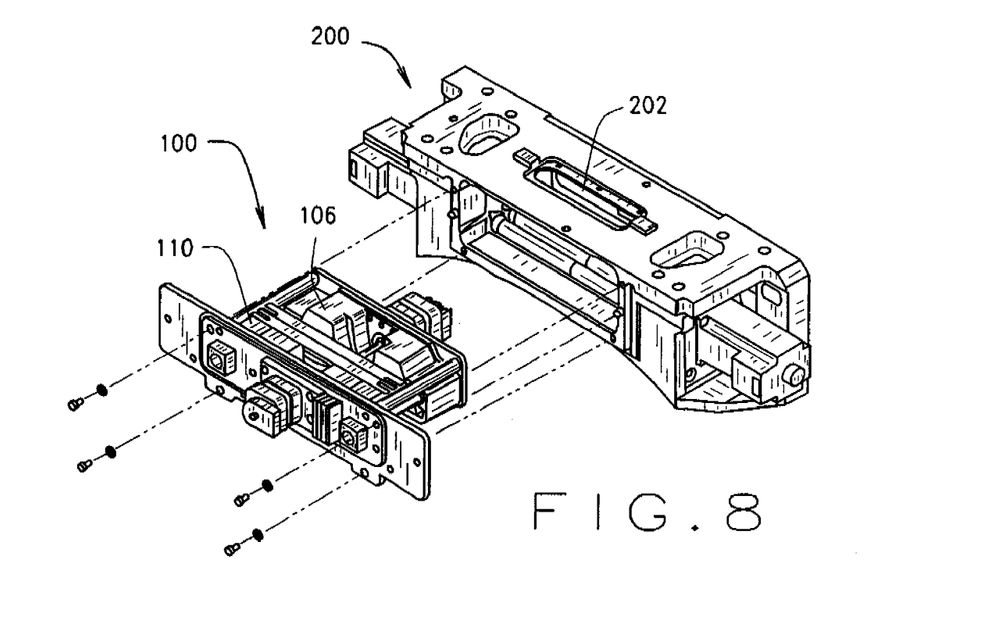
FIG. 8 is an exploded pictorial diagram illustrating the fitting of the filter assembly shown in FIG. 3 into a base assembly.

It will thus be recognized that a plurality of bowtie shapes and filters are available using filter assembly 100. In some configurations and referring to FIG. 8, filter assembly 100 is fitted into a base assembly 200, which is mounted on gantry 12. X-ray tube 14 produces an x-ray beam that passes through opening 202 to form a fan beam 16, which is further shaped by filter assembly 100 before passing out an opposite side of base assembly 202 and into gantry opening 48. By moving first moveable subassembly 106 and/or second moveable subassembly 110 into various positions, a plurality of bowtie and other filter shapes can be imparted to fan beam 16. For example, and referring to FIG. 5, a closed position 120 is provided in which flat plate 118 is interposed in front of x-ray fan beam 16, completely blocking x-rays from reaching an object 22. This position is useful, for example, during x-ray tube warm up.

Figure 9:
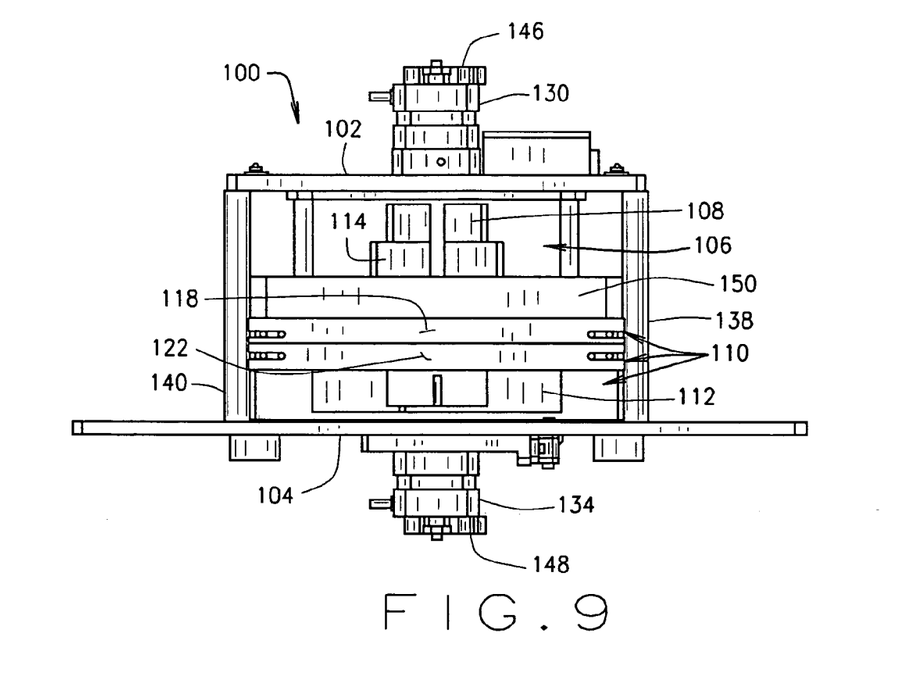
FIG. 9 is a top view of the filter assembly shown in FIG. 3 showing the filter assembly in an air position.
Figure 10:
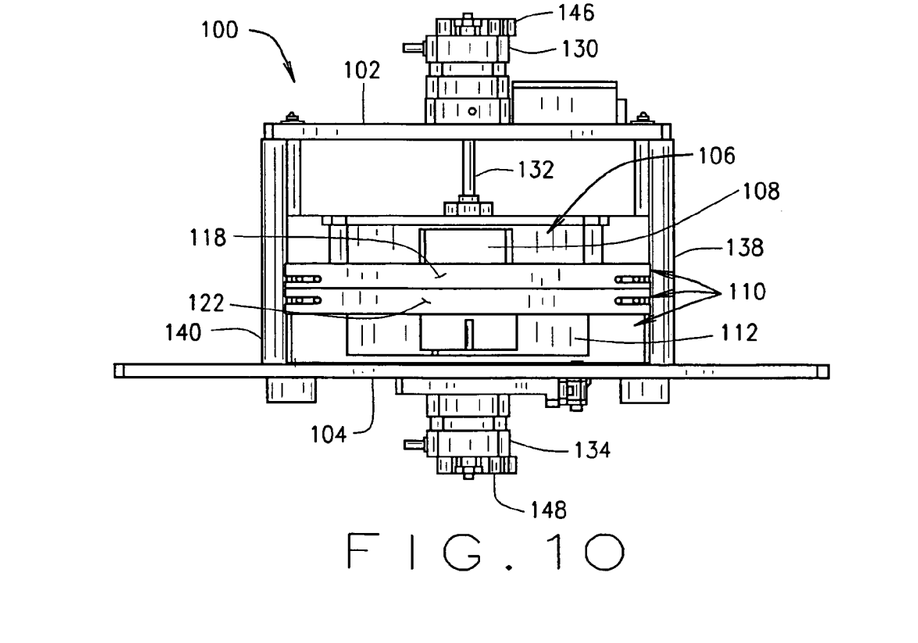
FIG. 10 is a top view of the filter assembly shown in FIG. 3 showing the filter assembly in a small bowtie filter position.
Figure 11:
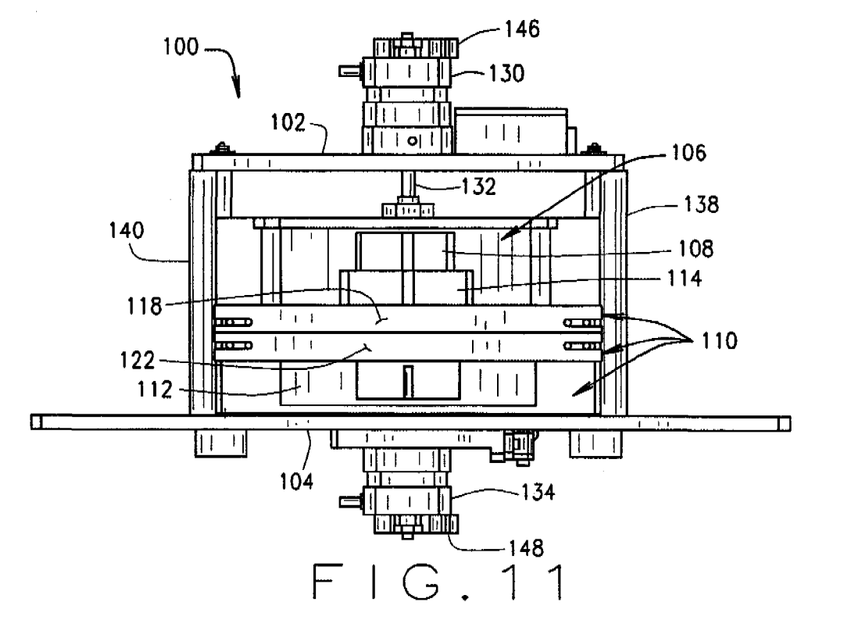
FIG. 11 is a top view of the filter assembly shown in FIG. 3 showing the filter assembly in a large filter position.
Figure 12:
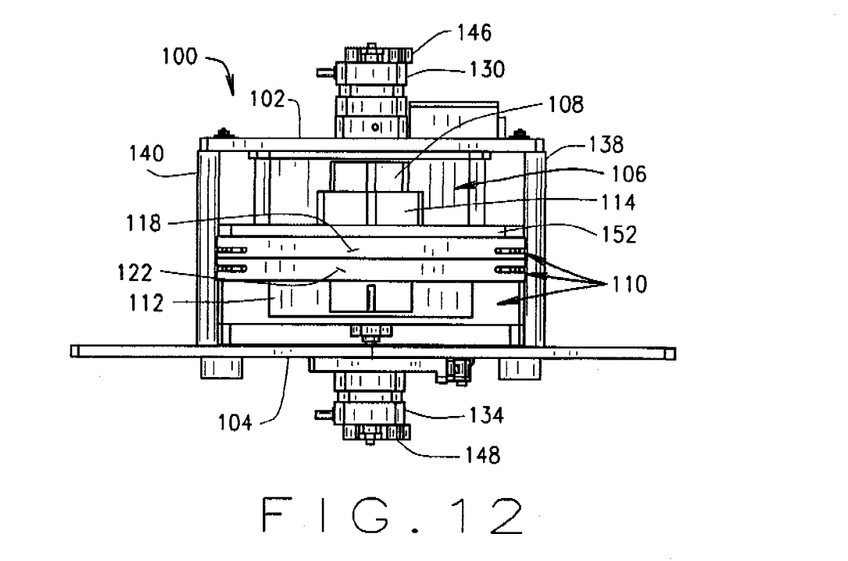
FIG. 12 is a top view of the filter assembly shown in FIG. 3 showing the filter assembly in a flat filter position.
Figure 13:
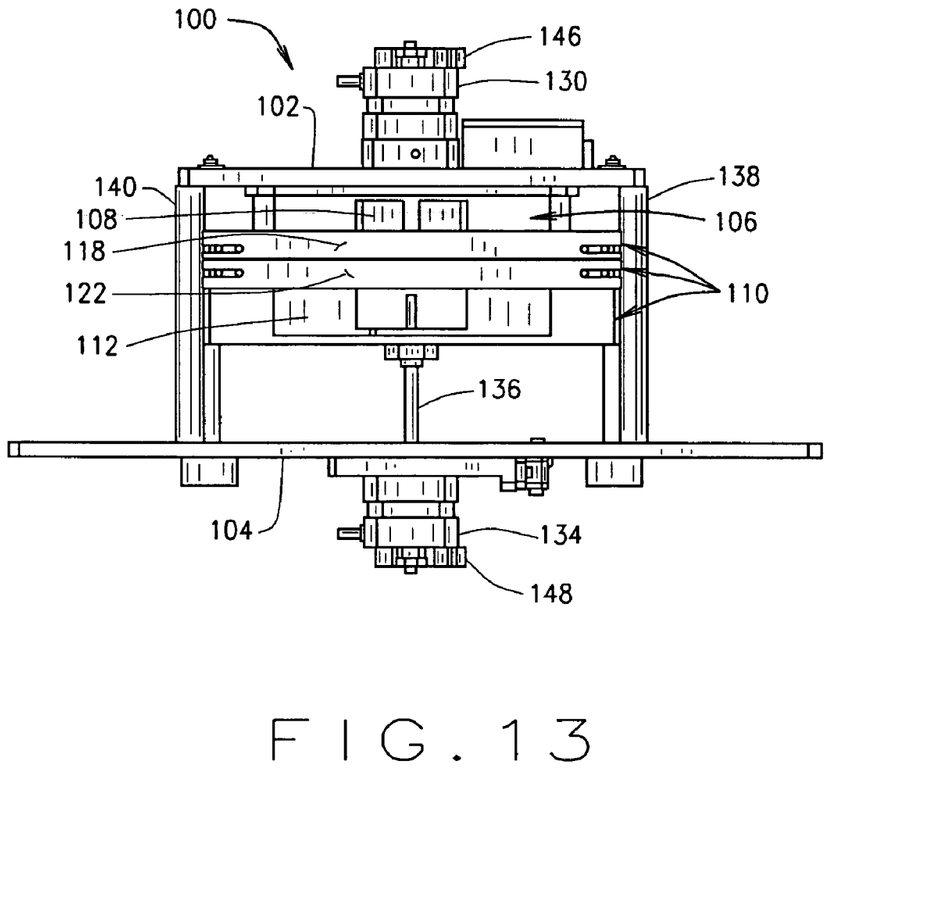
FIG. 13 is a top view of the filter assembly shown in FIG. 3 showing the filter assembly in a medium bowtie filter position.

In some configurations and referring to FIG. 9, an air position is provided into which first subassembly 106 and second subassembly 110 can be moved so that a clear path is provided through gap 150 in filter assembly 100 for x-ray beam 16. In yet another position and referring to FIG. 10, small bowtie filter 108 is interposed in the x-ray path. A patient's head can advantageously be imaged in this position, for example. In some configurations, in the position shown in FIG. 10, flat filter 118 overlaps large filter 114 to advantageously permit assembly 100 to provide a plurality of filter positions in a restricted volume allocated for assembly 100. In yet another position and referring to FIG. 11, large filter 114 is interposed in the x-ray path. This position can advantageously be used for imaging entire bodies, for example. In still another position and referring to FIG. 12, flat filter 118 is interposed in the x-ray path, represented as gap 152 in FIG. 12. This position can advantageously be used for imaging a large body, for example. In yet another position and referring to FIG. 13, a medium bowtie filter 112 is interposed in the x-ray path. This position can advantageously be used in pediatric imaging, for example. In some configurations, in this position, flat filter 118 also overlaps large filter 114.

Stepper motors 130 and 134 with lead screws 132 and 136, respectively, are used to drive the filters. A filter home switch (not shown in the Figures) is used to provide an absolute position reference and/or a home position reference. Incremental encoders 146 and 148 are used for position feedback. Lead nuts 170, which are pressed into or otherwise affixed on or into first subassembly 106 and second subassembly 110 also form part of the drive mechanisms.

Figure 6:
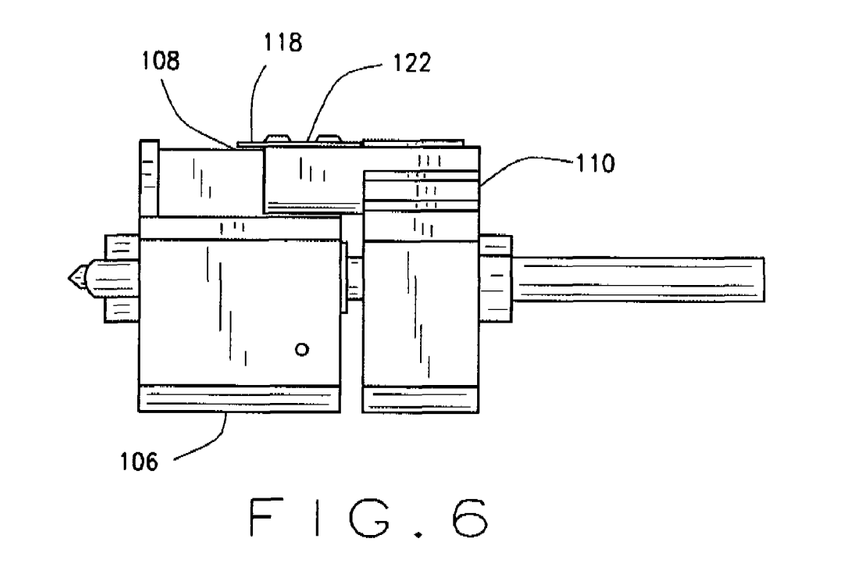
FIG. 6 is a side view of a portion of the filter assembly shown in FIG. 3 showing an overlap region of the filter subassemblies.
Figure 7:
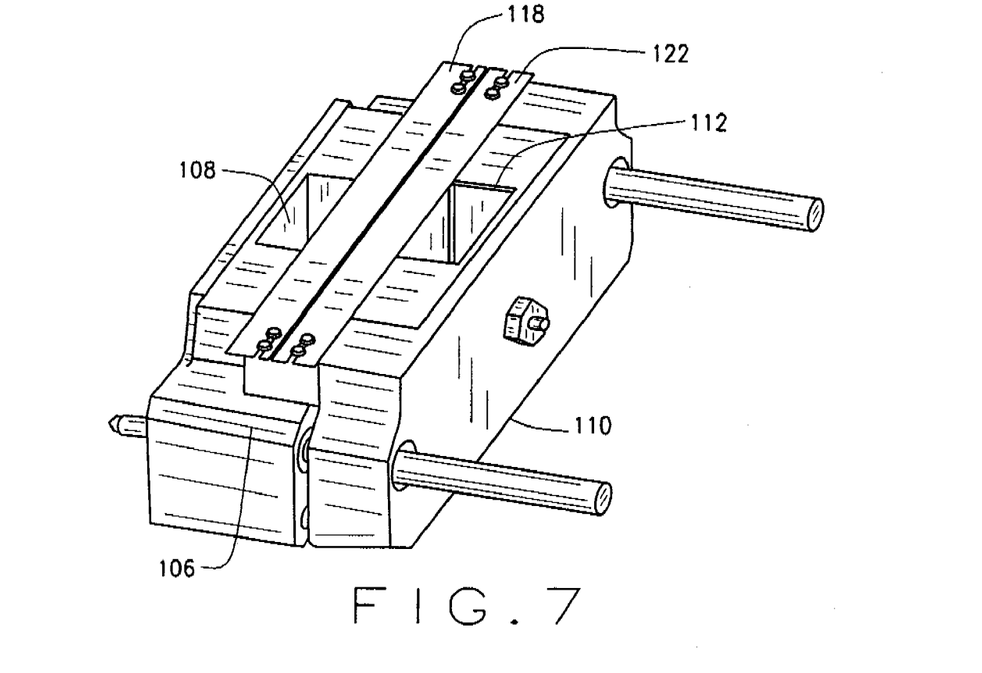
FIG. 7 is a oblique pictorial view of the portion of the filter assembly shown in FIG. 6.

The use of flat strips of titanium and tungsten for the large body (flat) filter and closed position rather than an aluminum and graphite combination helps to define an overlap, as shown in FIGS. 6 and 7.

The use of separate motors 130, 134 and encoders 146, 148 as part of the drive mechanism poses a challenge for cable routing. Because a printed circuit collimator control board is located close to a filter subassembly in some configurations, wires or cables 142 and 144 are routed back to front out of the X-Ray beam using, for example, stainless steel tubes 138 and 140. These tubes are used (in some configurations, in addition to other hardware 180) to connect endplates 102 and 104 to one another as well as for cable routing. (Additional hardware 180 also serves as a rail on which subassemblies 106 and 110 are guided in their movement.) Tubing 138 and 140 is positioned away from the x-ray beam to ensure that no artifacts are generated.

Subassemblies 106 and 110 can be moved independently of one another or simultaneously to reduce or minimize filter positioning time.

In some configurations of the present invention, filter assembly 100 is used in an imaging system 10 having a rotatable gantry 12 having a gantry opening 48. X-ray filter assembly 100 is mounted on rotatable gantry 12. Radiation source 14 is configured to direct a fan beam 16 of radiation towards an object or patient 22 in gantry opening 48 through x-ray filter assembly 100. Detector array 18 is on rotatable gantry 12 and is configured to acquire projection data representative of radiation passing through object 22, and imaging system 10 is configured to reconstruct an imaging of object 22 using the acquired projection data.

In some configurations, a method for filtering a radiation source 14 of a computed tomographic (CT) imaging system for scanning a region of an object 22 using a CT imaging system 10. The method includes passing a fan beam 16 of the radiation source between first and second endplates 102 and 104 of a filter assembly 100. Filter assembly 100 has a first moveable subassembly 106 comprising at least a first x-ray filter 108 configured to move along an axis z perpendicular to first endplate 102 and also perpendicular to a plane of fan beam 16 between first and second endplates 102 and 104. Filter assembly 100 also has a second moveable subassembly 110 comprising at least a second x-ray filter 112 configured to move along an axis z perpendicular to second endplate 104 and a plane of fan beam 16 between first and second endplates 102 and 104. The method further comprises moving at least one of first moveable subassembly 106 or second moveable subassembly 110 to interpose a small bowtie x-ray filter, a large bowtie x-ray filter, a medium bowtie x-ray filter, a flat filter, or a closed position between the radiation source and the object. In some configurations, the method further comprises overlapping at least one flat filter on the second moveable subassembly over a portion of a bowtie filter of the first moveable subassembly.

It will be appreciated that configurations of the present invention facilitate compact packaging of a plurality of filters. Moreover, filters are interchangeable with a minimum of design changes. Also, configurations of the present invention are easy to implement and cost effective.

While the invention has been described in terms of various specific embodiments, those skilled in the art will recognize that the invention can be practiced with modification within the spirit and scope of the claims.

What is claimed is:

1. A filter assembly for a computed tomographic imaging system comprising:
   first and second endplates at opposite ends of the filter assembly;
   a first moveable subassembly comprising at least a first x-ray filter and configured to move between said first and second endplates along a z-axis perpendicular to said first endplate;
   a second moveable subassembly comprising at least a second x-ray filter and configured to move between said first and second endplates along the z-axis perpendicular to said second endplate; and
   wherein said first moveable subassembly and said second moveable subassembly are independently movable along the z-axis to provide at least a small bowtie x-ray filter, a large bowtie x-ray filter, a medium bowtie x-ray filter, a flat filter, and a closed position for a radiation source positioned in a fixed position relative to said filter assembly, wherein the z-axis is parallel to a rotational axis of the computed tomographic imaging system.

2. A filter subassembly in accordance with claim 1 wherein said first movable subassembly comprises a small bowtie filter and the large bowtie filter, and the second movable subassembly comprises the medium bowtie filter.

3. A filter assembly in accordance with claim 2 wherein the second movable subassembly further comprises at least one flat filter.

4. A filter assembly in accordance with claim 3 wherein said at least one flat filter on said second movable subassembly is configurable to overlap a portion of one of said bowtie filters of said first movable subassembly in at least one position in a range of movement of said first movable subassembly and said second moveable subassembly.

5. A filter assembly in accordance with claim 3 wherein said at least one flat filter is a titanium plate.

6. A filter assembly in accordance with claim 5 wherein said at least one flat filter further comprises a plate of tungsten, and said bowtie filters of said first movable subassembly comprises a combination of aluminum and graphite machined parts and copper, and said bowtie filter of said second movable subassembly further comprises aluminum and graphite machined parts.

7. A filter assembly in accordance with claim 1 wherein said first movable subassembly and said second movable subassembly are independently movable and also simultaneously moveable.

8. A filter assembly in accordance with claim 1 further comprising a first stepper motor with lead screw drive configured to move said first moveable subassembly and a second stepper motor with lead screw drive configured to drive said second movable subassembly.

9. A filter assembly in accordance with claim 8 further comprising hollow tubing between the first and the second endplates configured to be outside an x-ray beam when in use, said hollow tubing having wires therein carrying electrical signals to at least one of said stepper motors.

10. A filter assembly in accordance with claim 8 further comprising a position encoder and a feedback control to provide a home position reference and position feedback.

11. A computed tomographic (CT) imaging system comprising:

a rotatable gantry having a gantry opening and a z-axis parallel to a gantry rotational axis;

an x-ray filter assembly on the rotatable gantry;

a radiation source configured to direct a fan beam of radiation towards an object in the gantry opening through the x-ray filter assembly; and a detector array on the rotatable gantry configured to acquire projection data representative of radiation passing through the object; wherein said CT imaging system configured to reconstruct an image of the object utilizing the acquired projection data; and said filter assembly further comprising:

first and second endplates at opposite ends of the filter assembly;

a first moveable subassembly comprising at least a first x-ray filter and configured to move between said first and second endplates along a z-axis perpendicular to said first endplate; and a second moveable subassembly comprising at least a second x-ray filter and configured to move between said first and second endplates along the z-axis perpendicular to said second endplate and perpendicular to a plane of said fan beam of radiation;

wherein said first moveable subassembly and said second moveable subassembly are independently movable along the z-axis to provide at least a small bowtie x-ray filter, a large bowtie x-ray filter, a medium bowtie x-ray filter, a flat filter, and a closed position for a radiation source positioned in a fixed position relative to said filter assembly.

12. A CT imaging system in accordance with claim 11 wherein said first movable subassembly comprises a small bowtie filter and the large bowtie filter, and the second movable subassembly comprises the medium bowtie filter.

13. A CT imaging system in accordance with claim 12 wherein the second movable subassembly further comprises at least one flat filter.

14. A CT imaging system in accordance with claim 13 wherein said at least one flat filter on said second movable subassembly is configurable to overlap a portion of one of said bowtie filters of said first movable subassembly in at least one position in a range of movement of said first movable subassembly and said second moveable subassembly.

15. A CT imaging system in accordance with claim 11 wherein said first movable subassembly and said second movable subassembly are independently movable and also simultaneously moveable.

16. A CT imaging system in accordance with claim 11 further comprising a first stepper motor with lead screw drive configured to move said first moveable subassembly and a second stepper motor with lead screw drive configured to drive said second movable subassembly.

17. A CT imaging system in accordance with claim 16 further comprising hollow tubing between the first and the second endplates configured to be outside the x-ray fan beam, said hollow tubing having wires therein carrying electrical signals to at least one of said stepper motors.

18. A CT imaging system in accordance with claim 16 further comprising a position encoder and a feedback control to provide a home position reference and position feedback for the first filter subassembly and the second filter subassembly.

19. A method for filtering a radiation source of a computed tomographic (CT) imaging system for scanning a region of an object using the CT imaging system, said method comprising:

passing a fan beam of the radiation source between first and second endplates at opposite ends of a filter assembly, the filter assembly having a first moveable subassembly comprising at least a first x-ray filter configured to move between said first and second endplates along a z-axis perpendicular to said first endplate and the fan beam, and a second moveable subassembly comprising at least a second x-ray filter configured to move between said first and second endplates along the z-axis perpendicular to said second endplate and the fan beam; and moving at least one of the first moveable subassembly or the second moveable subassembly along the z-axis to interpose a small bowtie x-ray filter, a large bowtie x-ray filter, a medium bowtie x-ray filter, a flat filter, or a closed position between the radiation source and the object, wherein the z-axis parallel to a rotational axis of the CT imaging system.

20. A method in accordance with claim 19 further comprising overlapping at least one flat filter on the second movable subassembly over a portion of a bowtie filter of the first movable subassembly.

21. A filter subassembly in accordance with claim 1 wherein said first endplate is other than said second endplate.

* * * * *